(12) United States Patent
Nagel et al.

(10) Patent No.: US 9,737,658 B2
(45) Date of Patent: Aug. 22, 2017

(54) STOPPER ARRANGEMENT FOR A DRUG DELIVERY DEVICE

(71) Applicant: SANOFI-AVENTIS DEUTSCHLAND GMBH, Frankfurt am Main (DE)

(72) Inventors: Thomas Nagel, Tharandt (DE); Rene Richter, Tharandt (DE); Robert Witt, Dresden (DE); Richard Guenther, Dresden (DE); Martin Graefe, Pirna (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 256 days.

(21) Appl. No.: 14/405,989

(22) PCT Filed: Jun. 25, 2013

(86) PCT No.: PCT/EP2013/063235
§ 371 (c)(1),
(2) Date: Dec. 5, 2014

(87) PCT Pub. No.: WO2014/001308
PCT Pub. Date: Jan. 3, 2014

(65) Prior Publication Data
US 2015/0148745 A1    May 28, 2015

(30) Foreign Application Priority Data
Jun. 27, 2012 (EP) .................................... 12173959

(51) Int. Cl.
*A61M 37/00* (2006.01)
*A61M 5/145* (2006.01)
*A61M 5/315* (2006.01)

(52) U.S. Cl.
CPC ...... *A61M 5/1452* (2013.01); *A61M 5/31511* (2013.01); *A61M 5/31515* (2013.01); *A61M 5/31501* (2013.01); *A61M 2205/10* (2013.01)

(58) Field of Classification Search
CPC ............ A61M 5/1452; A61M 5/31511; A61M 5/31515
See application file for complete search history.

(56) References Cited

U.S. PATENT DOCUMENTS

2003/0229310 A1    12/2003  Flaherty et al.
2005/0171476 A1*    8/2005  Judson .............. A61M 5/14566
                                                                         604/131
(Continued)

FOREIGN PATENT DOCUMENTS

CN          102448522        5/2012
JP          2007-127086 A    5/2007
(Continued)

OTHER PUBLICATIONS

Chinese Office Action for CN Application No. 201380030079.6, issued Jul. 5, 2016.
(Continued)

*Primary Examiner* — Edelmira Bosques
(74) *Attorney, Agent, or Firm* — McDonnell Boehnen Hulbert & Berghoff LLP

(57) ABSTRACT

The invention relates to a stopper arrangement for a drug delivery device, comprising a stopper, a linear actor coupled with one end to the stopper and with an opposite end to a coupling arrangement, wherein the stopper arrangement is configured to be disposed within a container of a drug delivery device, wherein a shape and/or material of the stopper and the coupling arrangement are configured such that a first frictional force between the coupling arrangement and the container is lower than a frictional force between the stopper and the container when the linear actor is contracting (Continued)

and that second frictional force between the coupling arrangement and the container is greater than the frictional force between the stopper and the container when the linear actor is expanding.

15 Claims, 1 Drawing Sheet

(56) References Cited

U.S. PATENT DOCUMENTS

2008/0300550 A1  12/2008  Schiller et al.
2012/0165783 A1*  6/2012  Wheatley ............ A61M 5/1452
                                                        604/506

FOREIGN PATENT DOCUMENTS

| WO | 2006/113521 A2 | 10/2006 |
| WO | 2007/116086 | 10/2007 |
| WO | 2010/115817 | 10/2010 |

OTHER PUBLICATIONS

International Search Report for Int. App. No. PCT/EP2013/063235, completed Oct. 9, 2013.
Japanese Office Action for JP Application No. 2015-519048, dated Apr. 4, 2017.

* cited by examiner

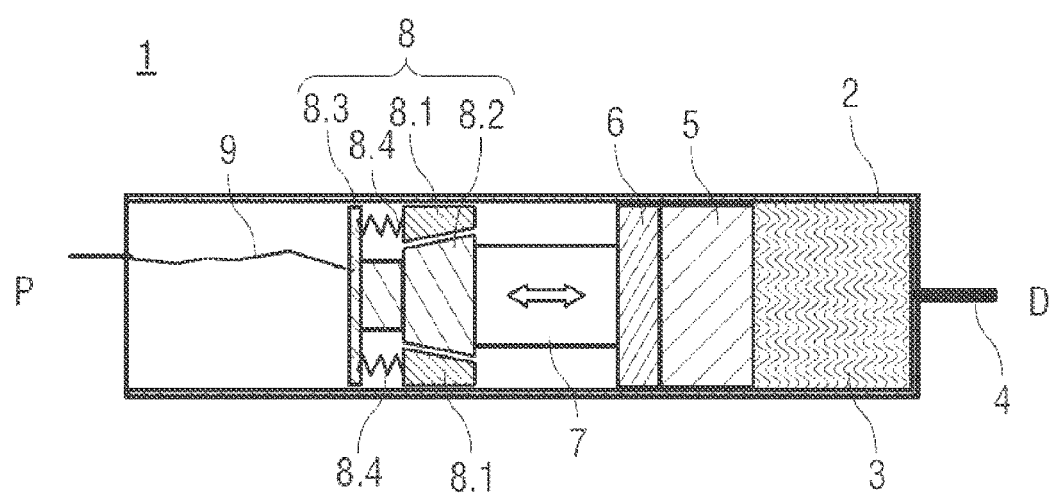

STOPPER ARRANGEMENT FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2013/063235 filed Jun. 25, 2013, which claims priority to European Patent Application No. 12173959.3 filed Jun. 27, 2012. The entire disclosure contents of these applications are herewith incorporated by reference into the present application.

TECHNICAL FIELD

The invention relates to a stopper arrangement for a drug delivery device.

BACKGROUND

Conventional drug delivery devices comprise a container defining a cavity within for retaining a drug, a nozzle, e.g. an injection needle arranged at a distal end of the container, wherein the nozzle is in fluid communication with the cavity, and a stopper with a plunger disposed in the container for displacing the drug.

U.S. 2008/0300550 A1 discloses a stopper adapted for attachment with a plunger rod for use within a syringe barrel. The stopper includes a main body defining an open rearward end and a closed front end. The open rearward end is adapted to receive a front forward end attachment portion of the plunger rod. The stopper also includes a core member integrally formed with said main body adjacent the closed front end. The core member includes a nose portion having a profile adapted to create a positive seal with an outlet opening of such syringe barrel.

SUMMARY

It is an object of the present invention to provide an improved stopper arrangement.

The object is achieved by a stopper arrangement according to claim 1.

Preferred embodiments of the invention are given in the dependent claims.

According to the invention a stopper arrangement for a drug delivery device comprises a stopper, a linear actor coupled with one end to the stopper and with an opposite end to a coupling arrangement, wherein the stopper arrangement is configured to be disposed within a container of a drug delivery device, wherein a shape and/or material of the stopper and the coupling arrangement are configured such that a first frictional force between the coupling arrangement and the container is lower than a frictional force between the stopper and the container when the linear actor is contracting and that second frictional force between the coupling arrangement and the container is greater than the frictional force between the stopper and the container when the linear actor is expanding.

The stopper arrangement according to the invention is self propelled thus allowing for drug delivery devices with a significantly reduced total length, as a plunger handle is not required.

The linear actor may be a high precision linear actor with a small adjustment range as the total adjustment range of the stopper may be partitioned into an arbitrary number of small steps by the described arrangement of the linear actor and the coupling arrangement.

In an exemplary embodiment the coupling arrangement may comprise at least one wedge block tapering towards a distal direction and a conical inner ring tapering towards a proximal direction, wherein the wedge block is arranged between the inner ring and the container, wherein the inner ring is attached proximally to a proximal plate and distally to the linear actor, wherein the coupling arrangement is configured to engage to the container with the first frictional force when the inner ring is not pressed against the at least one wedge block. When the linear actor is expanding, the inner ring is pressed against the at least one wedge block engaging the container thus increasing the amount of friction to the second frictional force. The first friction force comprises the force between the wedge blocks and the inner container wall when the coupling arrangement is pulled towards the stopper on contraction of the linear actor. The first frictional force may also comprise a frictional component of the proximal plate that may be in contact with the container. This may happen at least occasionally during movement of the coupling arrangement within the container.

The friction force of the stopper in the container is configured to be greater than the force required for releasing the coupling mechanism as well as the first friction force. However, the friction force of the stopper in the container is also configured to be smaller than the second frictional force of the coupling arrangement when the linear actor is expanding.

In an exemplary embodiment the inner ring may be replaced by a cone. However, the inner ring allows for a decreased length.

In an exemplary embodiment the wedge block is biased in the distal direction against the proximal plate by a respective biasing element, for example a spring arranged as a compression spring. The wedge block may likewise be held spaced from the proximal plate by notches or hooks instead of the spring. In an alternative embodiment, notches on the surface of the inner ring or hooks extending from the proximal end of the inner ring may be configured to hold the wedge block. Thus, a proximal plate is not required.

In an exemplary embodiment the linear actor comprises a solenoid.

In another exemplary embodiment the linear actor comprises an electric motor with a spindle and a nut.

In an exemplary embodiment a stopper plate is proximally attached to the stopper and the linear actor is attached to the stopper plate. The stopper plate may be releasably attached to the stopper, so that the stopper arrangement can be removed from the container. Thus the stopper arrangement can be reused while the container is disposed of so that the amount of waste and the environmental footprint is reduced.

An energy supply cable for controlling the linear actor may be run through the proximal plate and the inner ring. The linear actor could likewise be powered by a battery arranged in the stopper arrangement.

In an exemplary embodiment at least two wedge blocks are concentrically arranged around the inner ring.

The stopper arrangement may be employed in a drug delivery device, comprising a container defining a cavity within for retaining a drug, a nozzle arranged at a distal end of the container, wherein the nozzle is in fluid communication with the cavity, wherein the stopper arrangement is disposed in the container.

In an exemplary embodiment a removal aid for moving the wedge block or wedge blocks into a neutral position towards the proximal plate may be arranged. In order to reuse the linear actor and the coupling arrangement they have to be pulled out of the proximal end of the container. For this purpose the wedge blocks are moved into the neutral position towards the proximal plate against the bias of the springs so that they don't wedge to the wall of the container when the proximal plate and inner ring are pulled in the proximal direction.

In an exemplary embodiment the removal aid comprises a ring magnet externally arrangeable over the container.

In another exemplary embodiment the removal aid comprises at least one solenoid arranged on the inner ring or on the proximal plate.

In another exemplary embodiment the removal aid comprises a mechanical or magnetic tool insertable through a proximal end of the container.

Typically the container and the stopper have a cylindrical cross section. However, different cross sections, such as prismatic, rectangular, square or elliptical or likewise possible.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);

or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, -continued H-Asn-(Glu)5-des Pro36, Pro37, Pro38 [Asp28]
Exendin-4(1-39)-(Lys)6-NH2, H-(Lys)6-des Pro36 [Trp(O2)25, Asp28] Exendin-
4(1-39)-Lys6-NH2, H-des Asp28 Pro36, Pro37, Pro38 [Trp(O2)25]
Exendin-4(1-39)-NH2, H-(Lys)6-des Pro36, Pro37, Pro38 [Trp(O2)25, Asp28]
Exendin-4(1-39)-NH2, H-Asn-(Glu)5-des Pro36, Pro37, Pro38 [Trp(O2)25,
Asp28] Exendin-4(1-39)-NH2, des Pro36, Pro37, Pro38 [Trp(O2)25, Asp28] Exendin-
4(1-39)-(Lys)6-NH2, H-(Lys)6-des Pro36, Pro37, Pro38 [Trp(O2)25, Asp28]
Exendin-4(1-39)-(Lys)6-NH2, H-Asn-(Glu)5-des Pro36, Pro37, Pro38 [Trp(O2)25,
Asp28] Exendin-4(1-39)-(Lys)6-NH2, H-(Lys)6-des Pro36 [Met(O)14, Asp28] Exendin-
4(1-39)-Lys6-NH2, des Met(O)14 Asp28 Pro36, Pro37, Pro38 Exendin-
4(1-39)-NH2, H-(Lys)6-desPro36, Pro37, Pro38 [Met(O)14, Asp28]
Exendin-4(1-39)-NH2, H-Asn-(Glu)5-des Pro36, Pro37, Pro38 [Met(O)14,
Asp28] Exendin-4(1-39)-NH2, des Pro36, Pro37, Pro38 [Met(O)14, Asp28] Exendin-
4(1-39)-(Lys)6-NH2, H-(Lys)6-des Pro36, Pro37, Pro38 [Met(O)14, Asp28]
Exendin-4(1-39)-(Lys)6-NH2, H-Asn-(Glu)5 des Pro36, Pro37, Pro38 [Met(O)14,
Asp28] Exendin-4(1-39)-(Lys)6-NH2, H-Lys6-des Pro36 [Met(O)14, Trp(O2)25, Asp28]
Exendin-4(1-39)-Lys6-NH2, H-des Asp28 Pro36, Pro37, Pro38 [Met(O)14,
Trp(O2)25] Exendin-4(1-39)-NH2, H-(Lys)6-des Pro36, Pro37, Pro38 [Met(O)14, Asp28]
Exendin-4(1-39)-NH2, H-Asn-(Glu)5-des Pro36, Pro37, Pro38 [Met(O)14,
Trp(O2)25, Asp28] Exendin-4(1-39)-NH2, des Pro36, Pro37, Pro38 [Met(O)14, Trp(O2)25,
Asp28] Exendin-4(1-39)-(Lys)6-NH2, H-(Lys)6-des Pro36, Pro37, Pro38 [Met(O)14,
Trp(O2)25, Asp28] Exendin-4(S1-39)-(Lys)6-NH2, H-Asn-(Glu)5-des Pro36, Pro37, Pro38 [Met(O)14,
Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 is a schematic longitudinal-section of a drug delivery device.

DETAILED DESCRIPTION

FIG. 1 is a schematic longitudinal section of a drug delivery device 1. The drug delivery device 1 comprises a cylindrical container 2 defining a cavity 3 within for retaining a drug. A nozzle 4 is arranged at a distal end of the container 2, wherein the nozzle 4 is in fluid communication with the cavity 3. The nozzle 4 may be arranged as a hollow injection needle. The cavity 3 is proximally delimited by a cylindrical stopper 5 which may be axially moved within the container 2 for displacing the drug through the nozzle 4. A stopper plate 6 is proximally attached on the stopper 5. A linear actor 7 is arranged proximally from the stopper plate 6 so as to act between the stopper plate 6 and a coupling arrangement 8. The coupling arrangement 8 is arranged to be operatively coupled to the container 2. The coupling arrangement 8 comprises a number of wedge blocks 8.1 tapering towards a distal direction D and a cone or a conical inner ring, both schematically represented and designated as 8.2, tapering towards a proximal direction P, wherein the wedge blocks 8.1 are concentrically arranged around the cone or alternatively the conical inner ring 8.2, referred to hereinafter for brevity as just the inner ring.

The inner ring 8.2 is attached to a, e.g. cylindrical proximal plate 8.3 arranged proximally from the inner ring 8.2 and from the wedge blocks 8.1. The proximal plate 8.3 is disposed within the container 2. The coupling arrangement 8 is frictionally engaged to the wall of the container 2 with a first frictional force. The first frictional force between the coupling arrangement 8 and the container 2 wall is significantly lower than a frictional force between the stopper 5 and the container 2 wall. Each wedge block 8.1 is biased in the distal direction D against the proximal plate 8.3 by a respective spring 8.4 which is arranged as a relatively weak compression spring. The springs 8.4 may be attached to the proximal plate 8.3 and serve for reducing the wedge block 8.1 and the inner ring 8.2.

An energy supply cable 9 for the linear actor 7 is run through the proximal end of the container 2 and through the proximal plate 8.3 and the inner ring 8.2. Cable 9 also serves to control the movement of the linear actor 7. Alternatively, a battery is supplied in the coupling arrangement 8 to supply power to the linear actor 7. In this case, cable 9 is only used to provide control signals to the linear actor 7. In another example embodiment, the control signal is sent wirelessly to the linear actor, which in this case comprises a wireless transceiver. Thus, a cable is not required.

If the inner ring 8.2 is moved in the proximal direction P relative to the wedge blocks 8.1, e.g. by actuating the linear actor 7, the wedge blocks 8.1 and inner ring 8.2 become wedged to the wall of the container 2 thus switching the coupling arrangement 8 to have a second frictional force with respect to the container 2 wall, wherein the second frictional force is significantly greater than the frictional force between the stopper 5 and the container 2 wall. The proximal end of the linear actor 7 thus becomes grounded in the container 2 such that further expansion of the actor 7 breaks the stopper 5 loose off the container wall resulting in drug being displaced from the cavity 3 through the nozzle 4 depending on the amount of expansion of the actor 7. In an exemplary embodiment a ring with a conical inner surface tapering towards the distal direction D may be arranged instead of the wedge blocks 8.1. However, in this case the material of the ring needs to be elastic, such that the relation of the frictional forces can be provided.

The linear actor 7 may comprise a solenoid or an electric motor with a spindle and a nut.

The linear actor 7 may be arranged to expand and to contract depending on the way it is actuated.

The stopper plate 6 is attached to the stopper 5 such that on contraction of the linear actor 7 the distal end of the linear actor 7 becomes grounded in the container wall through the friction between the stopper 5 and the container 2 while the proximal end of the linear actor 7 pulls the inner ring 8.2 away from the wedge blocks 8.1 thus releasing the coupling arrangement 8. The friction force of the stopper 5 in the container 2 is significantly greater than the force required for releasing the coupling mechanism 8 as well as the friction force of the wedge blocks 8.1 in the container 2 when it is pulled towards the stopper 5 on contraction of the linear actor 7.

The connection between the stopper 5 and the stopper plate 6 may be releasable, e.g. by a snap-on coupling so as to make the linear actor 7 and the coupling arrangement 8 reusable. In order to reuse the linear actor 7 and the coupling arrangement 8 they have to be pulled out of the proximal end P of the container 2. For this purpose the wedge blocks 8.1 are moved into a neutral position towards the proximal plate 8.3 against the bias of the springs 8.4 so that they don't wedge to the wall of the container 2 when the proximal plate 8.3 and inner ring 8.2 are pulled in the proximal direction P. This positioning of the wedge blocks 8.1 may be achieved by a ring magnet (not illustrated) externally arranged or arrangeable over the container 2 or by a solenoid (not illustrated) arranged on the inner ring 8.2 or on the proximal plate 8.3. Or the wedge blocks 8.1 may be moved into the neutral position by mechanical or magnetic means inserted through the proximal end of the container 2.

In an exemplary embodiment the linear actor 7 and the coupling arrangement 8 are non-reusable or disposable. In this case the linear actor 7 can be attached directly to the stopper 5 so that the stopper plate 6 is not required.

The drug delivery device 1 may be applied for delivering liquid drugs such as proteins, vaccines, complex carbohydrates or growth hormones.

The linear actor 7 may be a high precision linear actor with a small adjustment range as the total adjustment range of the stopper may be partitioned into an arbitrary number of small steps by the described arrangement of the linear actor 7 and the coupling arrangement 8.

ment comprises at least one wedge block tapering towards a distal direction and a conical inner ring tapering towards a proximal direction, wherein the wedge block is configured to be arranged between the inner ring and the container, wherein the inner ring is attached proximally to a proximal plate and distally to the linear actor, wherein the coupling arrangement is configured to engage to the container with the first frictional force, wherein the inner ring and wedge block are configured to engage to the container when the linear actor is expanding thus increasing the amount of friction to the second frictional force.

2. The stopper arrangement according to claim 1, characterized in that the wedge block is biased in the distal direction against the proximal plate by a respective spring arranged as a compression spring.

3. The stopper arrangement according to claim 1, characterized in that the linear actor comprises a solenoid.

4. The stopper arrangement according to claim 1, characterized in that the linear actor comprises an electric motor with a spindle and a nut.

5. The stopper arrangement according to claim 1, characterized in that a stopper plate is proximally attached to the stopper and that the linear actor is attached to the stopper plate.

6. The stopper arrangement according to claim 5, characterized in that the stopper plate is releasably attached to the stopper.

7. The stopper arrangement according to claim 1, characterized in that an energy supply cable for controlling the linear actor is run through the proximal plate and the inner ring.

The invention claimed is:

1. A stopper arrangement for a drug delivery device, comprising a stopper, a linear actor coupled with one end to the stopper and with an opposite end to a coupling arrangement, wherein the stopper arrangement is configured to be disposed within a container of a drug delivery device, wherein a first frictional force between the coupling arrangement and the container is lower than a frictional force between the stopper and the container when the linear actor is contracting, wherein a second frictional force between the coupling arrangement and the container is greater than the frictional force between the stopper and the container when the linear actor is expanding, wherein the coupling arrange- 8. The stopper arrangement according to claim 1, characterized in that at least two wedge blocks are concentrically arranged around the inner ring.

9. A drug delivery device, comprising a container defining a cavity within for retaining a drug, a nozzle arranged at a distal end of the container, wherein the nozzle is in fluid communication with the cavity, wherein a stopper arrangement according to claim 1 is disposed in the container.

10. The drug delivery device according to claim 9, further comprising a removal aid for moving the wedge blocks into a neutral position towards the proximal plate.

11. The drug delivery device according to claim 10, wherein the removal aid comprises a mechanical or magnetic tool insertable through a proximal end of the container.

12. The drug delivery device according to claim 9, wherein the container and the stopper have a cylindrical cross section.

13. A stopper arrangement for a drug delivery device, comprising a stopper, a linear actor coupled with one end to the stopper and with an opposite end to a coupling arrangement, wherein the stopper arrangement is configured to be disposed within a container of a drug delivery device, wherein a first frictional force between the coupling arrangement and the container is lower than a frictional force between the stopper and the container when the linear actor is contracting, wherein a second frictional force between the coupling arrangement and the container is greater than the frictional force between the stopper and the container when the linear actor is expanding, wherein the coupling arrangement comprises at least one wedge block tapering towards a distal direction and a cone tapering towards a proximal direction, wherein the wedge block is configured to be arranged between the cone and the container, wherein the cone is attached proximally to a proximal plate and distally to the linear actor, wherein the coupling arrangement is configured to engage to the container with the first frictional force, wherein the cone and wedge block are configured to engage to the container when the linear actor is expanding thus increasing the amount of friction to the second frictional force.

14. A drug delivery device comprising:
a container defining a cavity within for retaining a drug;
a nozzle arranged at a distal end of the container, wherein the nozzle is in fluid communication with the cavity;
a stopper arrangement disposed in the container, wherein the stopper arrangement comprises a stopper, a linear actor coupled with one end to the stopper and with an opposite end to a coupling arrangement, wherein the stopper arrangement is configured to be disposed within a container of a drug delivery device, wherein a first frictional force between the coupling arrangement and the container is lower than a frictional force between the stopper and the container when the linear actor is contracting, wherein a second frictional force between the coupling arrangement and the container is greater than the frictional force between the stopper and the container when the linear actor is expanding, wherein the coupling arrangement comprises at least one wedge block tapering towards a distal direction and a conical inner ring tapering towards a proximal direction, wherein the wedge block is configured to be arranged between the inner ring and the container, wherein the inner ring is attached proximally to a proximal plate and distally to the linear actor, wherein the coupling arrangement is configured to engage to the container with the first frictional force, wherein the inner ring and wedge block are configured to engage to the container when the linear actor is expanding thus increasing the amount of friction to the second frictional force; and
a removal aid for moving the wedge blocks into a neutral position towards the plate, wherein the removal aid comprises a ring magnet externally arrangeable over the container.

15. A drug delivery device comprising:
a container defining a cavity within for retaining a drug;
a nozzle arranged at a distal end of the container, wherein the nozzle is in fluid communication with the cavity;
a stopper arrangement disposed in the container, wherein the stopper arrangement comprises a stopper, a linear actor coupled with one end to the stopper and with an opposite end to a coupling arrangement. wherein the stopper arrangement is configured to be disposed within a container of a drug delivery device, wherein a first frictional force between the coupling arrangement and the container is lower than a frictional force between the stopper and the container when the linear actor is contracting, wherein a second frictional force between the coupling arrangement and the container is greater than the frictional force between the stopper and the container when the linear actor is expanding, wherein the coupling arrangement comprises at least one wedge block tapering towards a distal direction and a conical inner ring tapering towards a proximal direction, wherein the wedge block is configured to be arranged between the inner ring and the container, wherein the inner ring is attached proximally to a proximal plate and distally to the linear actor, wherein the coupling arrangement is configured to engage to the container with the first frictional force, wherein the inner ring and wedge block are configured to engage to the container when the linear actor is expanding thus increasing the amount of friction to the second frictional force; and
a removal aid for moving the wedge blocks into a neutral position towards the proximal plate, wherein the removal aid comprises at least one solenoid arranged on the inner ring or on the proximal plate.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
        35
```